United States Patent
Thompson et al.

(10) Patent No.: US 9,537,344 B2
(45) Date of Patent: Jan. 3, 2017

(54) PHASE CHANGE MATERIAL AS A DYNAMIC HEAT SINK FOR TRANCUTANEOUS ENERGY TRANSMISSION SYSTEMS

(71) Applicant: CYBERONICS, INC., Houston, TX (US)

(72) Inventors: David L. Thompson, Houston, TX (US); Jeffrey B. Stewart, Tacoma, WA (US); Shan E. Gaw, Seattle, WA (US); John E. Rodriguez, Houston, TX (US); Charles A. Ritrivi, Houston, TX (US); Rajesh Ramesh, Houston, TX (US); Eric M. Lewis, Villa Park, CA (US)

(73) Assignee: CYBERONICS, INC., Houston, TX (US)

(*) Notice: Subject to any disclaimer, the term of this patent is extended or adjusted under 35 U.S.C. 154(b) by 214 days.

(21) Appl. No.: 14/185,855

(22) Filed: Feb. 20, 2014

(65) Prior Publication Data
US 2014/0233184 A1  Aug. 21, 2014

Related U.S. Application Data

(60) Provisional application No. 61/767,503, filed on Feb. 21, 2013.

(51) Int. Cl.
| | |
|---|---|
| *H05K 7/20* | (2006.01) |
| *H02J 7/02* | (2016.01) |
| *A61N 1/378* | (2006.01) |
| *H01M 10/6569* | (2014.01) |
| *H01M 10/613* | (2014.01) |
| *H01M 10/42* | (2006.01) |
| *H02J 7/00* | (2006.01) |

(52) U.S. Cl.
CPC .......... *H02J 7/025* (2013.01); *A61N 1/3787* (2013.01); *H01M 10/613* (2015.04); *H01M 10/6569* (2015.04); *H01M 2010/4278* (2013.01); *H01M 2220/30* (2013.01); *H02J 7/0042* (2013.01)

(58) Field of Classification Search
CPC ..... H02J 7/025; A61N 1/3787; H01M 10/613; H01M 10/6569; H01M 2220/30; H05K 7/20945
USPC ..................................................... 607/57, 61
See application file for complete search history.

(56) References Cited

U.S. PATENT DOCUMENTS

| | | |
|---|---|---|
| 5,545,191 A | 8/1996 | Mann et al. |
| 5,948,006 A | 9/1999 | Mann |

(Continued)

*Primary Examiner* — Bernard Rojas
(74) *Attorney, Agent, or Firm* — Foley & Lardner LLP

(57) ABSTRACT

A method and system for management of thermal energy produced during transcutaneous energy transmission to provide power to energize implanted medical devices. A phase changing material (PCM) acts as a heat sink to absorb thermal energy generated during the energy transfer process. The PCM can be thermally coupled to tissue proximate to an implanted medical device, enabling heat generated within the implantable device to be absorbed. The generation of heat during the energy transfer process is primarily caused by eddy currents induced in the implantable device by the magnetic flux produced by the energy transfer system. The PCM can also be used to absorb heat generated by the device producing the magnetic flux that is used to transcutaneously transfer electrical power to recharge a rechargeable power source or energize the implanted medical device.

7 Claims, 11 Drawing Sheets

(56) References Cited

U.S. PATENT DOCUMENTS

| | | | |
|---|---|---|---|
| 5,991,665 A | 11/1999 | Wang et al. | |
| 6,275,737 B1 | 8/2001 | Mann | |
| 6,324,430 B1 | 11/2001 | Zarinetchi et al. | |
| 7,225,032 B2 | 5/2007 | Schmeling et al. | |
| 7,505,816 B2 | 3/2009 | Schmeling et al. | |
| 7,738,965 B2* | 6/2010 | Phillips | A61N 1/3787 224/604 |
| 8,346,361 B2* | 1/2013 | Bauhahn | A61N 1/3787 607/32 |
| 8,974,366 B1* | 3/2015 | Radziemski | A61N 1/3787 600/16 |
| 2008/0303480 A1* | 12/2008 | Prutchi | H02J 7/025 320/108 |

* cited by examiner

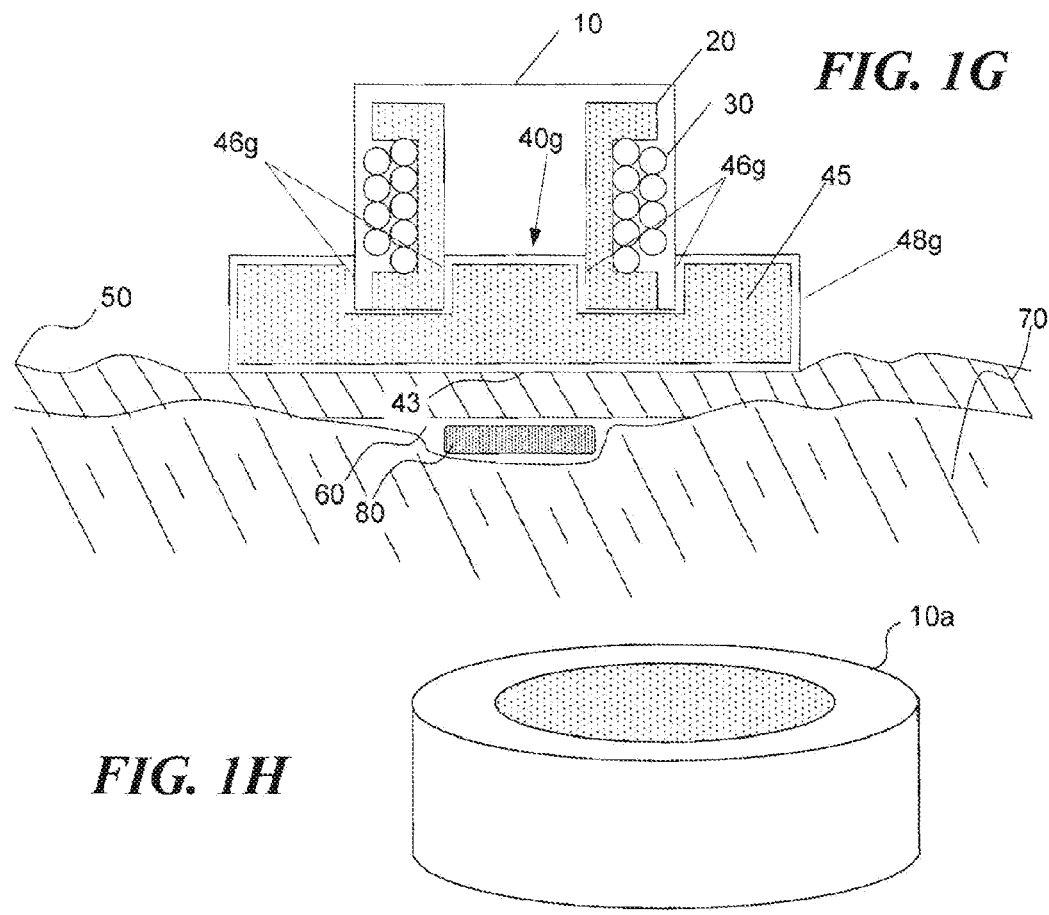
*FIG. 1G*
*FIG. 1H*
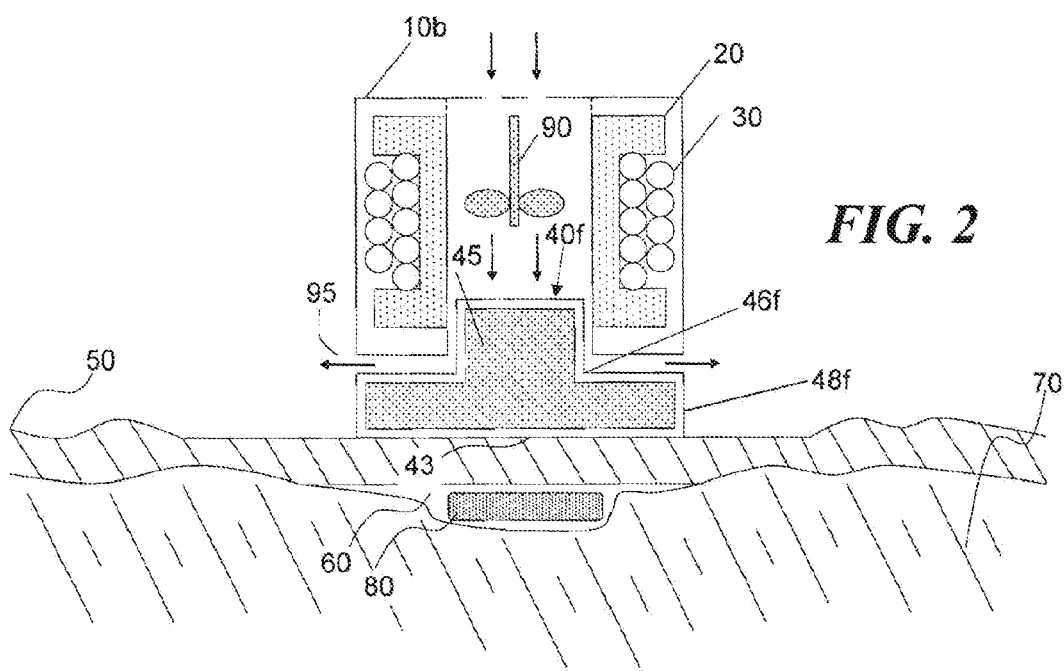
*FIG. 2*

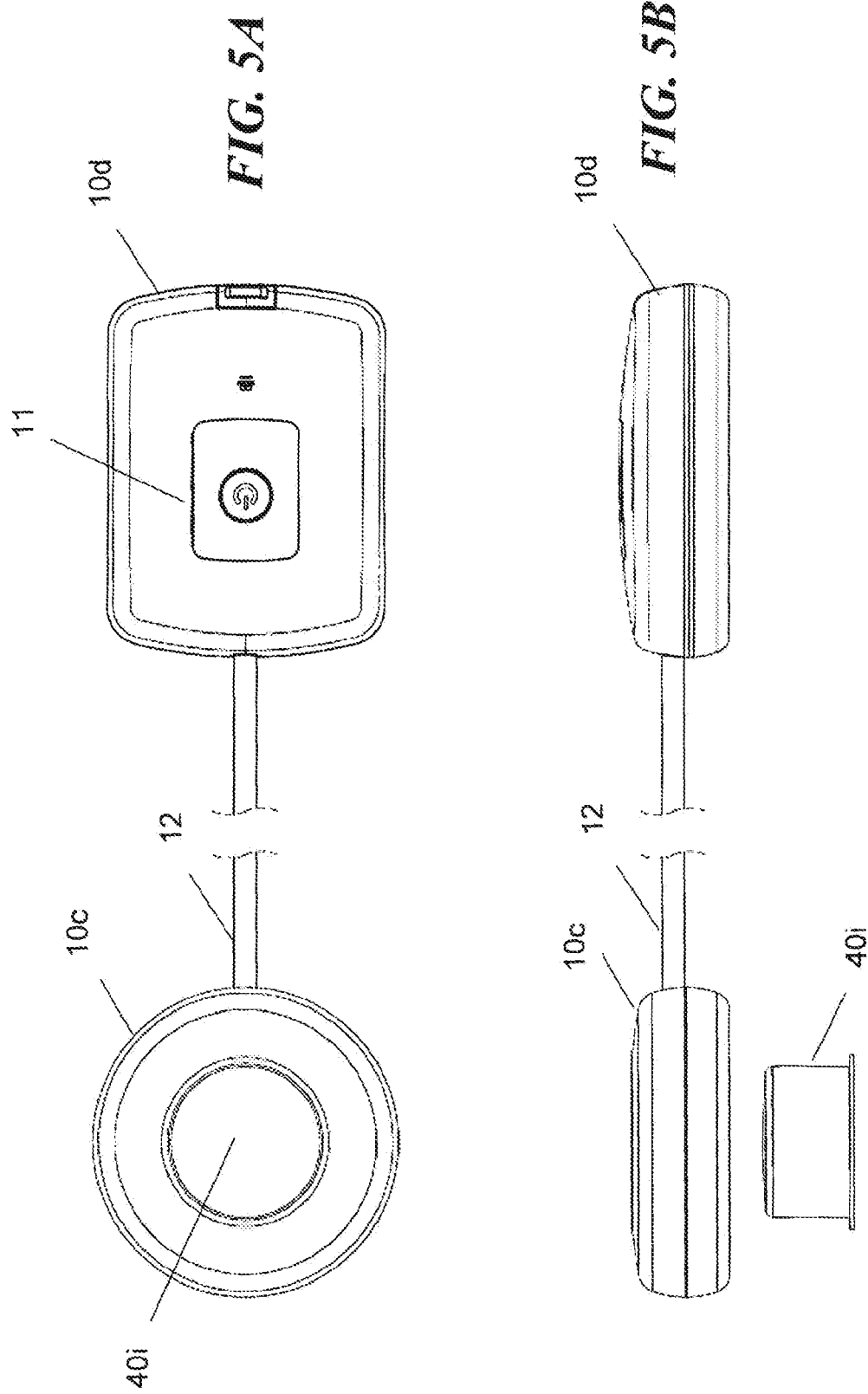

PHASE CHANGE MATERIAL AS A DYNAMIC HEAT SINK FOR TRANCUTANEOUS ENERGY TRANSMISSION SYSTEMS

CROSS REFERENCE TO RELATED APPLICATIONS

The present application claims the benefit of U.S. Provisional Application No. 61/767,503, filed Feb. 21, 2013, the complete disclosure of which is incorporated by reference herein in its entirety.

BACKGROUND

Many types of implantable medical devices require a source of electrical energy. For example, pacemakers, defibrillators, drug infusion pumps, cochlear implants, and brain activity monitoring/stimulation systems all require a power source. Many of these implantable medical devices provide therapy and/or diagnostic functions, and have significant electrical power requirements.

Electrical current used to supply the electrical power required by an implanted medical device can be conveyed through an electrical lead that is connected to the device and extends outside the patient's body for connection to an external power source. However, a transcutaneous lead that passes through the skin increases the risk of infection when left in place for an extended period. Implanted medical devices may also be powered by a non-rechargeable battery. However, replacement of such a battery subjects the patient to further surgery, and thus, may not be desirable, particularly if replacement is frequently necessary.

As an alternative to a non-rechargeable battery, an implanted rechargeable battery can be recharged by transcutaneously coupling power from an external source to an implanted receiver that is connected to the rechargeable battery. One of the more efficient recharging techniques employs an external transmission coil and an internal receiver coil, which are inductively coupled so that power can be conveyed from the transmission coil to the receiver coil. In this transcutaneous energy transmission (TET) approach, the external primary transmission coil is energized with alternating current (AC), producing a time varying magnetic field that passes through the patient's skin and induces a corresponding AC in the internal secondary receiving coil. The voltage induced in the receiving coil may then be rectified to provide direct current (DC) that is used to power the implanted medical device and/or charge a battery or other charge storage device (e.g., an ultra capacitor), which continues to energize the implanted medical device after the inductive supply of electrical power is terminated. This transcutaneous energy transmission work was originally pioneered by J. C. Schuder in 1961 (J. C. Schuder, H. E. Stephenson, and J. F. Townsend, "High level electromagnetic energy transfer through a closed chest wall," IRE International Convention Record 9, part 9, pp. 119-126, 1961).

One challenge in designing TET systems is that eddy currents are induced in the metallic components (such as the housing or printed circuit boards) of the implanted medical device. Such eddy currents can produce a generally undesirable temperature increase or heating of the implantable device. The amount of heat generated is generally a function of the amplitude and frequency of the magnetic flux used in the TET system.

Additional thermal challenges presented in TET systems are caused by the heat produced within the external transmission coil and its associated external enclosure. One problem is that temperature increases in the external transmission coil decreases the efficiency of the TET system. For example, heating of the primary coil increases the resistance of the windings, which serves to reduce the amount of power transferred to the implantable unit, thereby increasing the time required for recharging, resulting in further heating of the external transmission coil enclosure and the heating of the implanted medical device. A second problem is that as the external transmission coil heats up, such heat can be transferred to the external housing surrounding the coil. That housing is located proximal to the patient's skin nearest the implanted medical device, and such a temperature increase can increase the skin temperature.

Implanted medical devices are generally surrounded by tissue, which to a certain extent will conduct heat away from the device. However, implanted device temperatures exceeding safe thresholds may injure or permanently damage surrounding tissue. The ability of human tissue to withstand hyperthermic conditions is governed by a complex relationship of factors including tissue type, temperature, and exposure time. It would be desirable to provide a method and apparatus that reduces the risk of damaging adjacent tissue during the recharging of implanted medical devices when using TET. Furthermore, the amount of transmitted power is primarily limited by the heating of (i) the tissue surrounding the implanted device; (ii) the skin surface adjacent to the external charging device; and (iii) the temperature of the external charging device. Such aforementioned heating limits the amount of power that may be transferred by the TET system, which increases the time required for recharging. Since the patient is typically inconvenienced during the recharging period, it would be desirable to maximize the power rate of transfer while minimizing associated heating. Prospective techniques for accomplishing that may employ one or more of the following strategies: (1) minimizing the heat caused by induced eddy currents; (2) transferring heat away from the tissue surrounding the implantable medical device; (3) reducing the operating temperature of the external components of the TET system; and, (4) isolating any temperature elevation of the external components of the TET system from the tissue proximate the implanted medical device.

SUMMARY

The concepts disclosed herein encompass the use of a phase change material (PCM) adjacent to the external charging component of a TET system. The PCM may function as a heat sink for one or more of: (a) the skin and tissue surrounding the implanted medical device; and (b) the external transmission coil. In the case where the PCM functions as a heat sink for the skin and tissue surrounding the implanted medical device, the PCM minimizes the amount of thermal energy that is transferred from the external component of the TET system to the adjacent tissue, and absorbs heat from the skin and tissue surrounding the implanted medical device, which reduces the thermal load on the tissue. In the case where the PCM functions as a heat sink for the external transmission coil, the PCM serves to minimize the amount of thermal energy which is transferred from the external component of the TET system to the adjacent tissue, as well as to absorb heat from the primary transmission winding. A PCM is a substance exhibiting a relatively large latent heat of fusion which, during a phase transition, is capable of respectively absorbing or releasing a relatively large amount of thermal energy. Heat is absorbed when the material changes from a more-ordered state to a less-ordered state (e.g., from a solid to a liquid or gas, or from a liquid to a gas), and is released during the opposite phase change (e.g., from a gas to a solid or liquid, or from a liquid to a solid).

When PCMs reach the temperature at which they change phase (e.g., their phase transition temperature), they may absorb relatively large amounts of heat while maintaining an almost constant temperature. The PCM may continue to absorb heat without a significant rise in temperature until all the PCM material is transformed to another phase. In an exemplary embodiment in which a solid changes phase into a liquid, when the ambient temperature around a liquid material falls, the PCM solidifies, releasing its stored latent heat. A large number of PCMs are available for various temperature ranges from about −5° C. up to about 190° C. Within the human comfort range of about 20° C. to about 40° C., some PCMs are very effective. They can absorb from about 5 to about 14 times more heat per unit volume than conventional heat sink materials that do not experience a phase change.

PCMs can be grouped into three categories, including organic PCMs, inorganic PCMs, and composite PCMs (e.g., eutectic mixtures). Organic PCMs include fatty acids ($CH_3(CH_2)_{2n}COOH$) and paraffin waxes with hydrocarbon chains of between 14 and 22 carbon atoms ($C_nH_{2n+2}$), which have melting points (i.e., solid to liquid phase transition points) between about 6° C. and about 41° C. Specific waxes that can be used for this purpose include (but are not limited to): eicosane (with a chain of twenty carbon atoms having a melting point of 36.6° C.) octadecane (with a chain of eighteen carbon atoms having a melting point of 28.1° C.), and hexadecane (with a chain of sixteen carbon atoms having a melting point of 18° C.). The first two of those three exemplary waxes experience only about a 7% density change during the liquid-to-solid transition, which represents one of the lower density changes of a PCM and is advantageous with respect to packaging considerations. An additional advantage of using such waxes as a PCM is that there is minimal chance of phase separation, since tests have been conducted to phase-cycle such materials as many as 30,000 times without any shift in their thermal capacity. Inorganic PCM materials include: hydrated salts (such as zinc nitrate, which melts at 36.2° C.) and anhydrous salts (such as meta phosphoric acid $HPO_4$ and Glaubers salt ($Na_2SO_4\ 10H_2O$), which changes phase at 32.2° C.).

PCMs can also be encapsulated within capsules such as 3-mm spherical beads. Such macro capsule PCMs are available through Microtek Laboratories, Inc. (Dayton, Ohio), and are used in cooling vests or garments. The macro capsule PCM particles are used to regulate the body temperature of individuals who work in hot environments, e.g. soldiers in a desert setting. The macro capsule PCMs absorb excess heat and permit the user to function for a longer time at a more comfortable temperature.

Thus, one aspect of the concepts disclosed herein is a TET system, including an external charging accessory (ECA) and a PCM, where the system is adapted for energizing an implanted medical device. The ECA includes an induction coil for transferring energy to the implanted medical device. The PCM is generally adjacent to the ECA, and may be in contact with the patient's skin or clothing. In some embodiments, the PCM is configured to remove heat from tissue proximate the implanted medical device, such heat having been generated by eddy currents induced in the implanted medical device during recharging. The PCM can also be thermally coupled to the ECA, to function as a heat sink for thermal energy produced by the ECA. Alternatively, the PCM material can be thermally isolated from the ECA (for example, by using a non-thermally conductive PCM membrane, an air gap, or a non-thermally conductive ECA housing), so as to reserve the PCM material to act as a heat sink only for the patient's tissue, as opposed to acting as a heat sink for both the patient's tissue as well as the ECA. In at least one exemplary embodiment, the PCM is encapsulated in a housing separate from that of the ECA. In a related exemplary embodiment, the PCM is disposed between the ECA and the patient.

The PCM material may be contained within a housing and/or membrane, in order to contain liquid or gas formed when the PCM material undergoes a phase change from a solid to a liquid or gas, or from a liquid to a gas. However, in order to eliminate the need for manufacturing a leak-resistant housing or membrane, in at least one embodiment disclosed herein such PCM macro capsules are encapsulated within a thermally conductive epoxy, which would eliminate the need for a PCM housing material.

Additionally, the use of PCM material is not limited to a single phase transition point (e.g., a single melting point or a single sublimation point). In some embodiments, a mixture of two or more PCM materials having different transition points may be used in order to optimize the heat accumulation properties.

This Summary has been provided to introduce a few concepts in a simplified form that are further described in detail below in the Description and illustrated in the accompanying Drawings. The Summary is not intended to limit the scope of the invention, which is defined solely by the claims attached hereto.

BRIEF DESCRIPTION OF THE DRAWINGS

FIG. 1G is a cross-sectional view of another exemplary embodiment of a self-cooling TET, illustrating a PCM heat accumulation structure that is both disposed within the cylindrical volume defined by the toroidal shape of the external ECA housing containing the primary coil of the ECA and surrounding an outer portion of the ECA housing, and is further disposed between the ECA and the patient.

FIG. 1H shows an exemplary toroidal shaped external ECA housing including a hollow central volume.

FIG. 2 is a cross-sectional view of the embodiment of FIG. 1F, with the addition of a fan that is configured to remove thermal energy accumulated by the PCM.

FIG. 5A is a top-view of an embodiment in which the primary coil is spaced apart from the ECA.

FIG. 5B is a side-view of the embodiment of FIG. 5A, also showing the PCM heat accumulation structure, which has been removed from the inside hollow central volume of the ECA.

DESCRIPTION

Figure 1A:
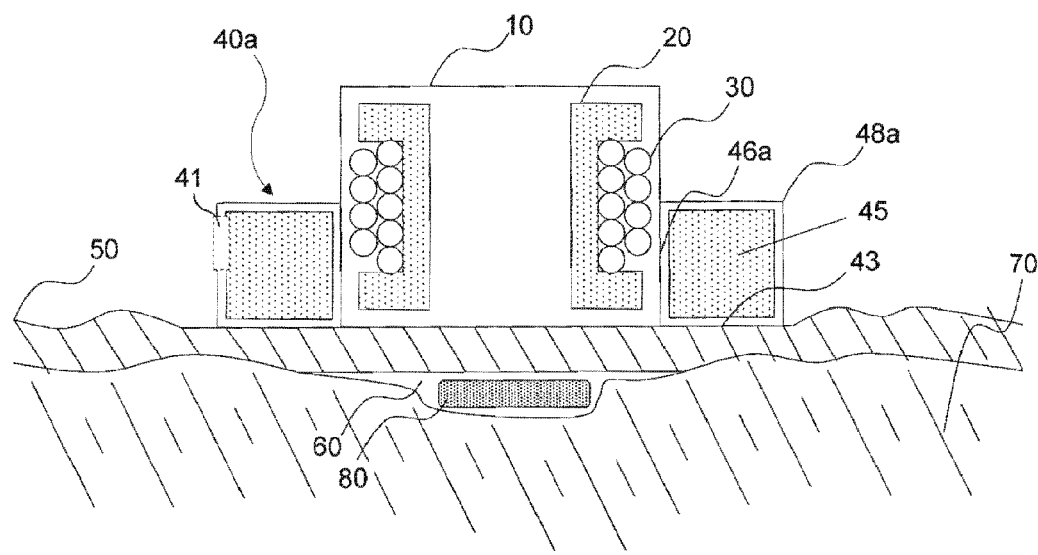
FIG. 1A is a cross-sectional view of an exemplary embodiment of a self-cooling TET system including an ECA and a cylindrical PCM heat accumulation structure thermally coupled to the patient's skin and surrounding a portion of an exterior of the ECA, where the ECA is being used to transfer energy to an implanted medical device.

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

In the drawings described below, reference numerals are generally repeated where identical elements appear in more than one Figure.

FIG. 1A is a cross-sectional view of an exemplary embodiment of a self-cooling TET system including an ECA 10, a PCM heat accumulation structure 40a that is thermally coupled to the patient's skin and generally surrounding a portion of an exterior of the ECA that is being used to transfer energy to an implanted medical device 80. It should be recognized that in some embodiments, an implantable medical device will be considered as part of the present system (e.g., in embodiments where the ECA, PCM heat accumulation structure, and implantable medical device are sold as a package), while in some other embodiments, the implantable medical device will not be considered as part of the system (e.g., in embodiments where the ECA and PCM heat accumulation structure are sold separately from the implantable medical device).

The ECA includes an outer housing, a bobbin 20 (e.g., a spindle or cylindrical core), and a primary induction coil 30, contained within a common housing (although as will be discussed in greater detail below, if desired, the components can be disposed of in different housings). The ECA transfers electromagnetic energy to implanted medical device 80 (shown disposed within a subcutaneous pocket 60 that is formed between a dermal layer 50 underlying muscular tissue 70).

Figure 3:
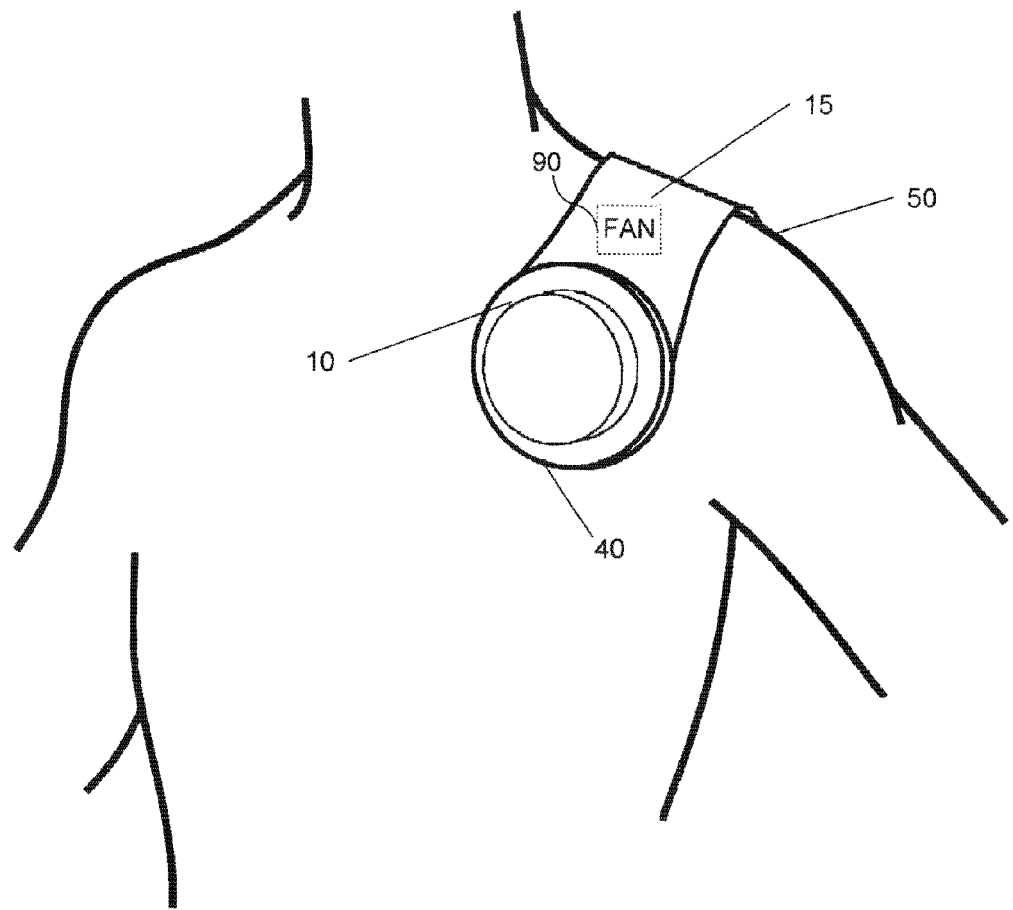
FIG. 3 illustrates a patient and shows a strap or harness that may be attached to the patient to secure the ECA and the PCM heat accumulation structure in a desired position.

During the charging process, ECA 10 is placed on the patient's body (either directly contacting the patient's dermal layer or a relatively thin layer of clothing). The charger may simply rest upon the patient's body, with the patient in a generally supine or sitting position, or the housing may be held in position relative to the patient via a strap or harness 15, as illustrated in FIG. 3. The strap enables a patient to be ambulatory, assuming that the ECA is battery operated, or in the case where the ECA is powered via an electrical outlet, the ambulatory state will be subject to limitations of any power supply line providing electrical energy to the ECA during the energy transfer process. If desired, a thermally conductive adhesive pad (or non-thermally conductive, for the case where the PCM is only being used as a dynamic heat sink for the ECA and not the skin—thereby thermally isolating the skin from the ECA) may be used to temporarily hold ECA 10 in place against dermal layer 50, in addition to, or in lieu of harness 15.

Primary induction coil 30 within ECA 10 produces an alternating magnetic field, which couples to the secondary coil (not separately shown) within implanted medical device 80, inducing an alternating current (AC) to flow within the secondary coil. The induced AC is then rectified producing a direct current (DC) that is used to charge the rechargeable energy source (e.g., a rechargeable battery or capacitor, also not shown) within implanted medical device 80. The magnetic flux also induces eddy currents on and within metallic portions of implanted medical device 80, causing undesired heating. The heat generated within implanted medical device 80 is conducted to tissue 70, causing a temperature rise to occur. In order to prevent tissue 70 from being heated to an undesirable temperature (e.g., above a potentially damaging threshold of about 42° C.), a PCM heat accumulation structure 40a is disposed proximate dermal layer 50, to function as a heat sink for thermal energy generated in implanted medical device 80. In the exemplary embodiment illustrated in FIG. 1A, PCM heat accumulation structure 40a also functions as a heat sink for thermal energy generated by ECA 10. Thus, PCM heat accumulation structure 40a is configured to surround at least a portion of an external housing of ECA 10. FIG. 5B illustrates a solid model of the ECA and the PCM heat accumulation structure, where the PCM heat accumulation structure has been removed from the central volume defined by the primary induction coil in the external charging unit.

The PCM heat accumulation structure 40a has a housing/enclosure 48a that is separate and distinct from ECA 10, such that once PCM heat accumulation structure 40a has absorbed a maximum amount of thermal energy so as to completely change its state, it can be removed and replaced with a unit whose PCM is still in a solid state (or still in a liquid state). This replacement may be accomplished easily without excessive disruption to the charging process. While it would be possible to integrate the PCM heat accumulation structure and the ECA in a common housing, the use of separate enclosures represents a desirable (but not limiting) embodiment. PCM heat accumulation structure 40a includes a volume of PCM 45 contained within enclosure 48a, which can be implemented using a variety of materials. For example, enclosure 48a can be either a rigid material or a flexible material which may conform to the patient's body. Different portions of enclosure 48a can be formed from different materials. A portion 43 of enclosure 48a proximate dermal layer 50 can be formed of a thermally conductive material to allow thermal energy to be conducted away from tissue 70 and towards PCM 45. Such thermally conductive material may include but are not limited to thermally conductive elastomers marketed under the trade name Cool Poly™, and thermally conductive co-polyester elastomers. The PCM acts as a heat sink, adsorbing thermal energy generated in the implanted medical device, effectively maintaining the adjacent tissue temperature below the 42° C. threshold, so long as the PCM selected has an appropriate phase transition point.

The optimal phase-transition temperature of PCM 45 is above the normal ambient temperature at which PCM heat accumulation structure 40a is stored when the TET system is not being used for supplying power or recharging a storage component in an implanted medical device, to ensure that PCM 45 is in the solid phase (or liquid phase) before use, so that the PCM is able to absorb thermal energy during the TET charging periods. (It will be understood that the PCM absorbs thermal energy as it undergoes a phase transition, e.g., melts or changes from a solid to a liquid, vaporizes from a liquid to a gas, or sublimates from a solid to a gas.) In some applications, it is desirable that the phase transition temperature of the PCM be less than the 42° C. threshold. For example, the phase transition temperature of the PCM can range from about 30° C. to about 42° C.

Given the volume and type of PCM selected, PCM heat accumulation structure 40a will exhibit an upper thermal capacity limit. Once the thermal capacity is met (meaning that the entire mass of PCM 45 will have undergone a phase change from, e.g., solid to liquid), PCM heat accumulation structure 40a will no longer function as an effective heat sink, but will instead continue increasing in temperature. Replacing a spent PCM heat accumulation structure 40a with a fresh PCM heat accumulation structure 40a will enable continued operation of the TET system by enabling the fresh PCM to absorb more heat before the temperature exceeds the desired limit. In at least one exemplary embodiment, each PCM heat accumulation structure 40a will include an optional feature 41 enabling a user to determine if the phase change (e.g., from solid to liquid) has occurred and has gone to completion. A simple feature that provides this functionality can be a window enabling the user to visually observe the phase change. More sophisticated features can provide a sensor and an alarm, such as a visible light or audible tone alerting the user that the PCM heat accumulation structure 40a is spent. It should be recognized that such a feature can be incorporated into any of the exemplary embodiments disclosed herein. Further, the specific location of feature 41 in the PCM heat accumulation structure shown in FIG. 1A is intended to be exemplary, rather than limiting.

Given the large variance in ambient temperatures throughout the world, it is also possible to have multiple PCM devices optimized for different ambient temperatures. Furthermore, for medical device implants which are located deeper within the patient's body, longer charging times will be required, therefore PCM devices having larger thermal capacities may also be offered. For example, in areas of higher ambient temperatures (such as the Southeastern United States), in order for a PCM to remain in a pre-transition form (e.g., a solid form) at an elevated ambient temperature, one might select a melting point closer to 42° C. than 30° C. On the other hand, if one expected the charging time to be long (due to a deep implant or a low battery level) one could select a PCM that had a low phase transition point (e.g. 15° C.), which would likely require the PCM to be stored in a refrigerator (or some other environment which is cooler than the ambient operating temperature) prior to use.

In at least some embodiments, a portion 46a of enclosure 48a proximate ECA 10 is formed of a thermally conductive material to allow thermal energy to be conducted away from ECA 10 and towards PCM 45. This configuration enables the ECA to run cooler and operate efficiently (electrical components in the ECA also can generate undesired thermal energy; for example, the primary winding generates heat as AC current runs through the winding, and the overall efficiency of the TET system decreases). However, the thermal capacity of the PCM will then be reached more quickly, since the PCM will be absorbing thermal energy from both the implanted medical device and the ECA. In at least one embodiment, to reserve the thermal absorbing capacity of PCM 45 for the purposes of absorbing thermal energy from tissue 70 (and not from ECA 10), portion 46a can be formed from a thermally insulating material. Alternatively, an air gap (not specifically shown, although it should be recognized that reference numeral 46a can be understood to indicate such an air gap, as opposed to a portion of enclosure 48a) can be disposed between ECA 10 and PCM heat accumulation structure 40a.

In an alternative embodiment, the thermal capacity of the PCM may be exclusively reserved for absorbing thermal energy from the ECA. In such an embodiment, portion 43 of enclosure 48a proximate dermal layer 50 can be formed of a thermally non-conductive material, to prevent thermal energy from being conducted away from tissue 70 and towards PCM 45, and/or an air gap can be disposed between the PCM and the skin.

Figure 1B:
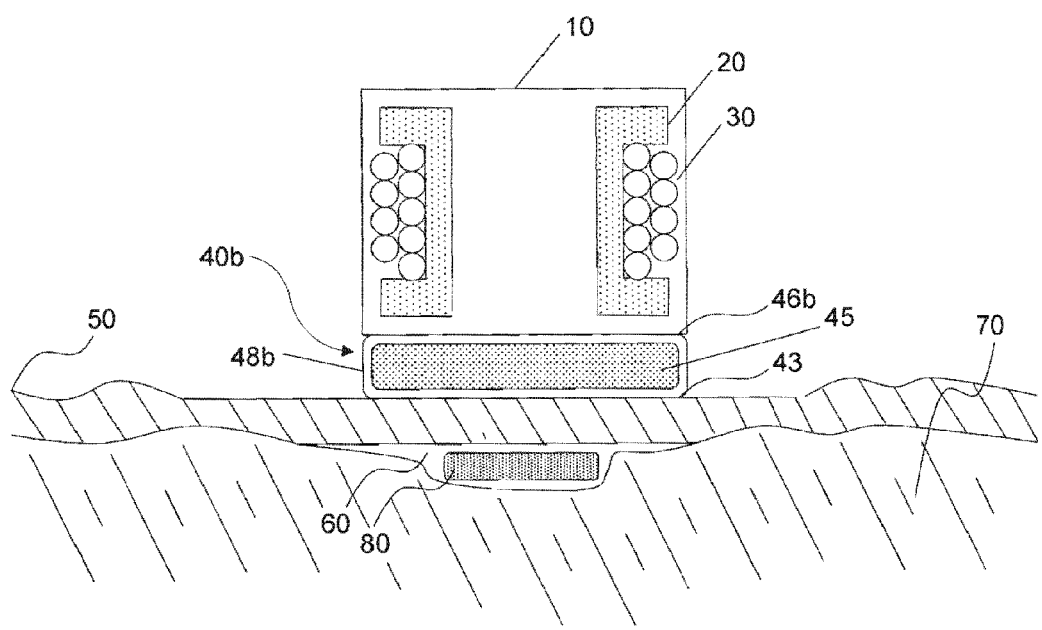
FIG. 1B is a cross-sectional view of another exemplary embodiment of a self-cooling TET system in which the PCM heat accumulation structure is disposed between the ECA and the patient.

FIG. 1B is a cross-sectional view of another exemplary embodiment of a self-cooling TET system in which a PCM heat accumulation structure 40b is disposed between ECA 10 and dermal layer 50 of the patient. In this embodiment, portion 43 of enclosure 48b (the portion proximate dermal layer 50) may be formed out of a thermally conductive material. If the thermal capacity of PCM 45 is to be dedicated to absorbing thermal energy from implanted medical device 80, then either portion 46b of enclosure 48b can be formed of a thermally insulating material, or an air gap can be incorporated into the system proximate portion 46b, generally as described above. Alternatively, the housing for ECA 10 can be made of thermally insulating material. It should be recognized that combinations and permutations of these techniques and the use of other types of thermal insulation can be employed to prevent the thermal capacity of the PCM from being used to absorb heat from ECA 10. Of course, portion 46b of enclosure 48b can instead be formed of a thermally conductive material, such that PCM heat accumulation structure 40b can be used to absorb heat both from ECA 10 and implanted medical device 80.

Additionally, if the thermal capacity of PCM 45 is to be exclusively dedicated to absorbing thermal energy from ECA 10, then either portion 43 of enclosure 48b (the portion proximate dermal layer 50) can be formed of a thermally insulating material, or an air gap can be incorporated between PCM enclosure 48b and dermal layer 50.

Figure 1C:
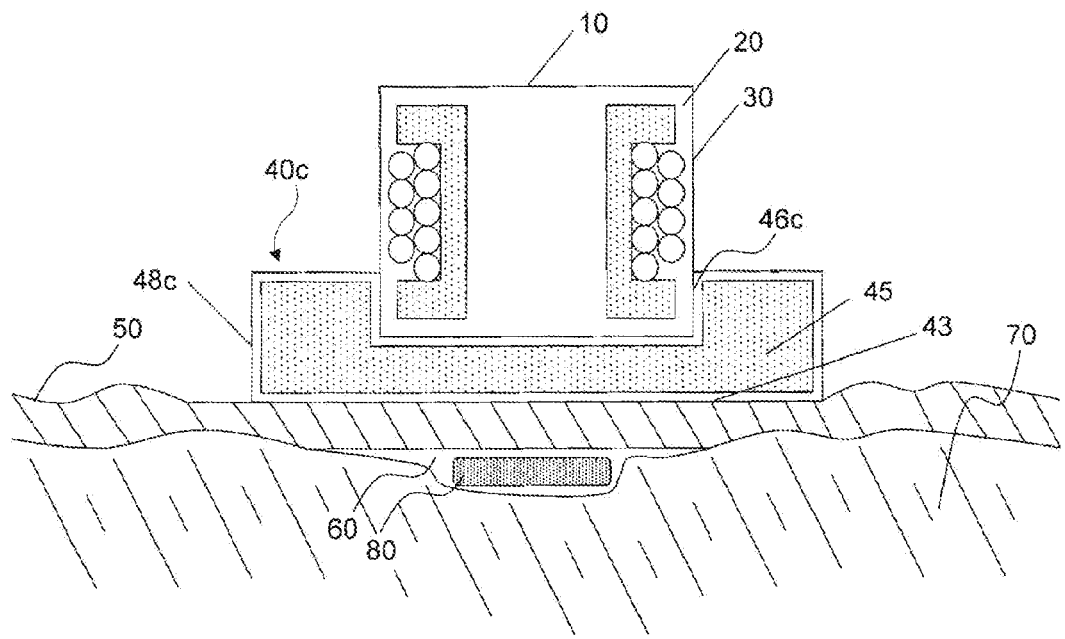
FIG. 1C is a cross-sectional view of still another exemplary embodiment of a self-cooling TET transfer system illustrating a PCM heat accumulation structure that combines features of the embodiments of FIGS. 1A and 1B, in that the PCM heat accumulation structure both generally surrounds the ECA and is disposed between the ECA and the patient.

FIG. 1C is a cross-sectional view of still another exemplary embodiment of a self-cooling TET transfer system illustrating a PCM heat accumulation structure 40c that combines features of the exemplary embodiments of FIGS. 1A and 1B, in that PCM heat accumulation structure 40c both generally surrounds ECA 10 and is disposed between the ECA and dermal layer 50 of the patient. As discussed above, if the thermal capacity of PCM 45 is to be dedicated to absorbing thermal energy from implanted medical device 80 and associated surrounding tissue, then either portion 46c of PCM enclosure 48c can be formed of a thermally insulating material, or an air gap can be incorporated into the system proximate portion 46c, or the housing for ECA 10 can be made of thermally insulating material. Again, it should be recognized that combinations and permutations of these techniques can be used to prevent the thermal capacity of the PCM from being used to absorb heat from ECA 10. Similarly, portion 46c of enclosure 48c can instead be formed of a thermally conductive material, such that PCM heat accumulation structure 40c can be used to absorb heat both from ECA 10 and implanted medical device 80 and associated surrounding tissue.

Additionally, if the thermal capacity of PCM 45 is to be exclusively dedicated to absorbing thermal energy from ECA 10, then either portion 43 of enclosure 40c (the portion proximate dermal layer 50) can be formed of a thermally insulating material, or an air gap can be incorporated between PCM enclosure 48c and dermal layer 50.

Figure 1D:
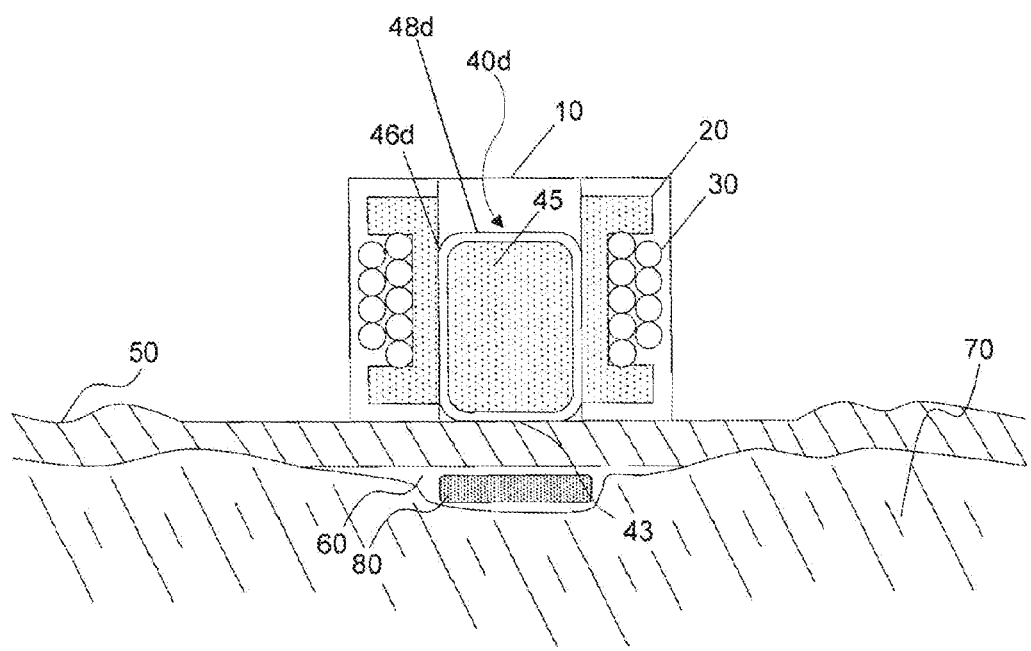
FIG. 1D is a cross-sectional view of another exemplary embodiment of a self-cooling TET, illustrating a PCM heat accumulation structure disposed within a cylindrical volume defined by the toroidal shape of the external ECA housing containing the primary coil.

FIG. 1D is a cross-sectional view of another exemplary embodiment of a self-cooling TET system illustrating a PCM heat accumulation structure 40d disposed within a volume defined by primary coil 30 of ECA 10 (note in such an embodiment, the housing for ECA 10 is toroidal in shape, and the cylindrical cavity defined by the toroidal housing provides the cavity in which PCM heat accumulation structure 40d is disposed). If the finite thermal capacity of PCM heat accumulation structure 40d is to be reserved for absorbing thermal energy from implanted medical device 80 and surrounding tissue (as opposed to also absorbing thermal energy from ECA 10), a thermally non-conductive material can be used for a portion 46d of enclosure 48d, or for the housing of ECA 10, or an air gap can be disposed between the ECA and the PCM heat accumulation structure, generally as discussed above. If PCM heat accumulation structure 40d is intended to both absorb thermal energy from ECA 10 and the implanted medical device and surrounding tissue, then portion 46d can instead be implemented using a thermally conductive material.

Additionally, if the thermal capacity of PCM 45 is to be exclusively dedicated to absorbing thermal energy from ECA 10, then either portion 43 of enclosure 40d (the portion proximate dermal layer 50) can be formed of a thermally insulating material, or an air gap can be incorporated between PCM enclosure 48d and dermal layer 50.

Figure 1E:
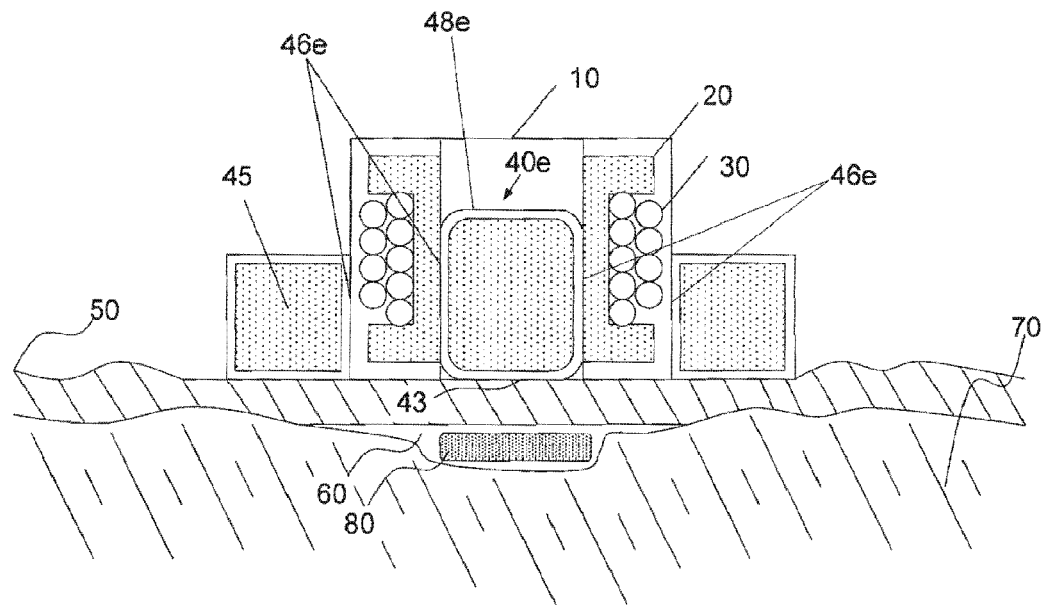
FIG. 1E is a cross-sectional view of another exemplary embodiment of a self-cooling TET, illustrating a PCM heat accumulation structure disposed within the cylindrical volume defined by the toroidal shape of the external ECA housing containing the primary coil.

FIG. 1E is a cross-sectional view of another exemplary embodiment of a self-cooling TET system, illustrating a PCM heat accumulation structure 40e, coupled to the exterior of ECA 10 specifically within a toroidal volume defined by primary coil 30 of ECA 10 and also generally surrounding a portion of an exterior of ECA 10. This embodiment combines the elements of the exemplary embodiments illustrated in FIGS. 1A and 1D. If PCM heat accumulation structure 40e is to be reserved for absorbing thermal energy from implanted medical device 80 and surrounding tissue (as opposed to also absorbing thermal energy from ECA 10), the techniques discussed above can be used to thermally isolate the ECA from the PCM. If PCM heat accumulation structure 40e is instead intended to absorb thermal energy from ECA 10, then portions 46e of enclosure 48e can be fabricated using a thermally conductive material.

Additionally, if the thermal capacity of PCM 45 is to be exclusively dedicated to absorbing thermal energy from ECA 10, then either portion 43 of enclosure 40e (the portion proximate dermal layer 50) can be formed of a thermally insulating material, or an air gap can be incorporated between PCM enclosure 48e and dermal layer 50.

Figure 1F:
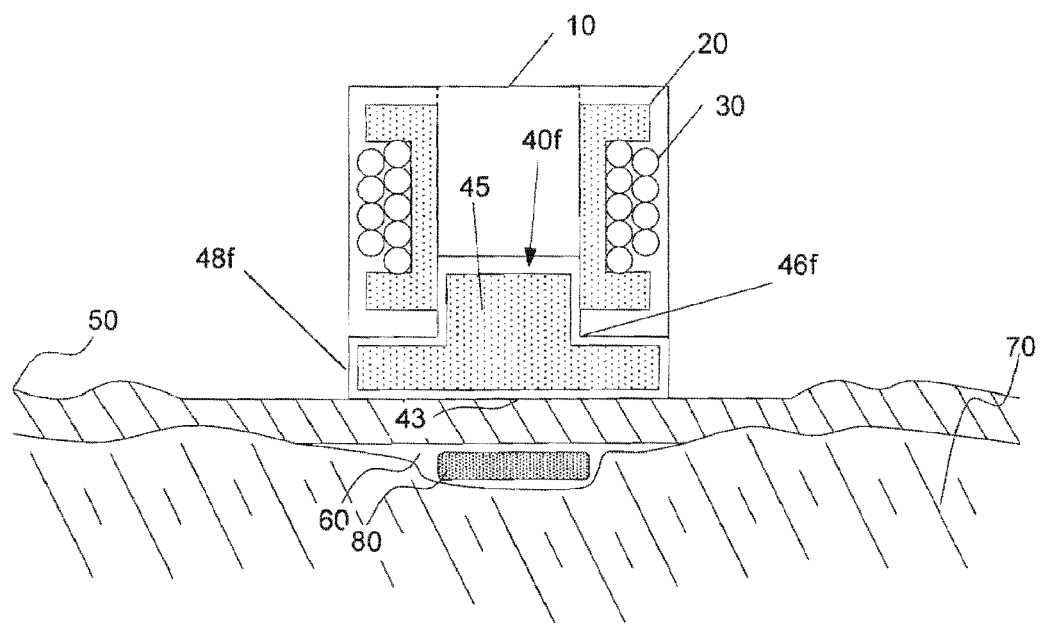
FIG. 1F is a cross-sectional view of another exemplary embodiment of a self-cooling TET, illustrating a PCM heat accumulation structure disposed within the cylindrical volume defined by the toroidal shape of the external ECA housing containing the primary coil of the ECA and also disposed between the ECA and the patient.

FIG. 1F is a cross-sectional view of another exemplary embodiment of a self-cooling TET system, illustrating a PCM heat accumulation structure 40f disposed on an exterior of ECA 10 specifically within a volume defined by primary coil 30 of ECA 10 and also disposed between the ECA and dermal layer 50 of the patient. This embodiment combines the elements of the exemplary embodiments illustrated in FIGS. 1B and 1D. If PCM heat accumulation structure 40f is to be reserved for absorbing thermal energy from implanted medical device 80 (as opposed to also absorbing thermal energy from ECA 10), the techniques discussed above can be used to thermally isolate the ECA from the PCM. If PCM heat accumulation structure 40f is intended to instead absorb thermal energy from ECA 10, then portion 46f of enclosure 48f can be fabricated using a thermally conductive material.

Additionally, if the thermal capacity of PCM 45 is to be exclusively dedicated to absorbing thermal energy from ECA 10, then either portion 43 of enclosure 40f (the portion proximate dermal layer 50) can be formed of a thermally insulating material, or an air gap can be incorporated between PCM enclosure 48f and dermal layer 50.

FIG. 1G is a cross-sectional view of another exemplary embodiment of a self-cooling TET system, illustrating a PCM heat accumulation structure 40g that is disposed externally of ECA 10; specifically simultaneously being disposed partially within a volume defined by a portion of the ECA housing covering a primary coil of the ECA, being disposed to partially surround a portion of an exterior of the ECA, and being disposed between the ECA and the patient. This exemplary embodiment combines the elements of the exemplary embodiments illustrated in FIGS. 1C and 1D. If PCM heat accumulation structure 40g is to be reserved for absorbing thermal energy from implanted medical device 80 (as opposed to also absorbing thermal energy from ECA 10), the techniques discussed above can be used to thermally isolate the ECA from the PCM. If PCM heat accumulation structure 40g is instead intended to absorb thermal energy from ECA 10, then portions 46g of enclosure 48g can be fabricated using a thermally conductive material.

Additionally, if the thermal capacity of PCM 45 is to be exclusively dedicated to absorbing thermal energy from ECA 10, then either portion 43 of enclosure 40g (the portion proximate dermal layer 50) can be formed of a thermally insulating material, or an air gap can be incorporated between PCM enclosure 48g and dermal layer 50.

FIG. 1H shows an exemplary toroidal shaped external ECA housing 10a including a hollow central volume. A PCM heat accumulation structure can be configured to fit partially or entirely, within the hollow central volume, to partially or entirely encircle an outer periphery of ECA housing 10a, and/or combinations thereof.

FIG. 2 is a cross-sectional view of the embodiment of FIG. 1F, in which an ECA 10b includes a cooling fan 90 disposed to remove thermal energy accumulated by PCM 45. The fan serves to transport ambient air 95 over the PCM so as to transport some heat away from the PCM, as the PCM is absorbing heat from the patient's tissue. Transporting some heat away from the PCM will increase the effective heat absorption capacity of the PCM, enabling increased cooling capacity. This fan configuration can also be implemented in any of the PCM heat accumulation structure embodiments illustrated in FIGS. 1A, 1B, 1C, 1D, 1E, and 1G.

FIG. 3 schematically illustrates a strap 15 (or harness) that may be attached to a patient to secure ECA 10 and PCM heat accumulation structure 40 in proper position relative to the patient's dermal layer 50. If desired, the cooling fan 90 of FIG. 2 can be incorporated into the harness, rather than into the ECA. Similar to the fan, the PCM structure may also be incorporated into the strap/harness for the ECA.

Figure 4:
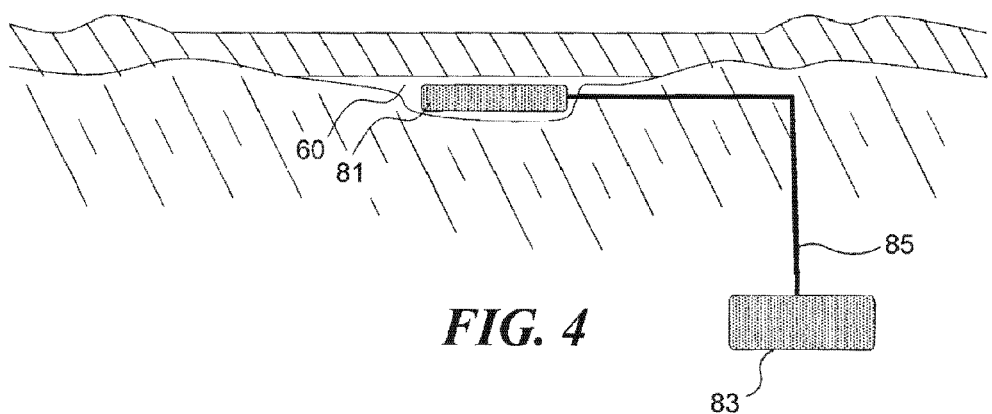
FIG. 4 illustrates an embodiment in which the secondary coil implanted within the patient is spaced apart from the implanted medical device.

FIG. 4 schematically illustrates an embodiment in which a secondary coil 81 implanted within a patient is spaced apart from an implanted medical device 83, and one or more conductors 85 couples the secondary coil to implanted medical device 83. In the embodiments discussed above, the secondary coil disposed to receive energy from the primary induction coil within ECA 10 was considered to be part of implanted medical device 80. The embodiment of FIG. 4 recognizes that while the secondary coil itself does need to be disposed proximate a location accessible to the ECA, the implanted medical device (or elements of the implanted medical device) can be disposed at other locations, so long as those other elements requiring energy are electrically coupled to the secondary coil. Thus, it should be understood that the concepts disclosed herein apply to embodiments in which the secondary coil is spaced apart from (but electrically coupled to) one or more elements of the implanted medical device.

FIG. 5A schematically illustrates a top-view of an embodiment in which a primary transmission coil of an external charging unit is contained within its own housing 10c, which is spaced apart from the other remaining electrical components of the external charging unit contained within a separate housing 10d, and one or more conductors 12 electrically couples together the components contained in housings 10c and 10d. In previously presented embodiments discussed above, the primary transmission coil is configured to transmit energy to the secondary coil in the implanted medical device, and the additional electrical components in the ECA were considered to be disposed in a common housing. The embodiment of FIG. 5A recognizes that while the primary coil is disposed proximate to the implanted secondary receiving coil, other electrical components of the ECA may be positioned at a different location, so long as those electrical components are connected to the primary coil by one or more electrical conductors. Thus, it should be understood that the concepts disclosed herein apply to embodiments in which the primary coil is spaced apart from (but electrically coupled to) one or more elements electrical elements required by the ECA.

FIG. 5B schematically illustrates a side-view of FIG. 5A. It should be noted that PCM heat accumulation structure 40i is illustrated as being removed from inside a central toroidal volume defined by housing 10c of the external charging accessory.

Figure 6A:
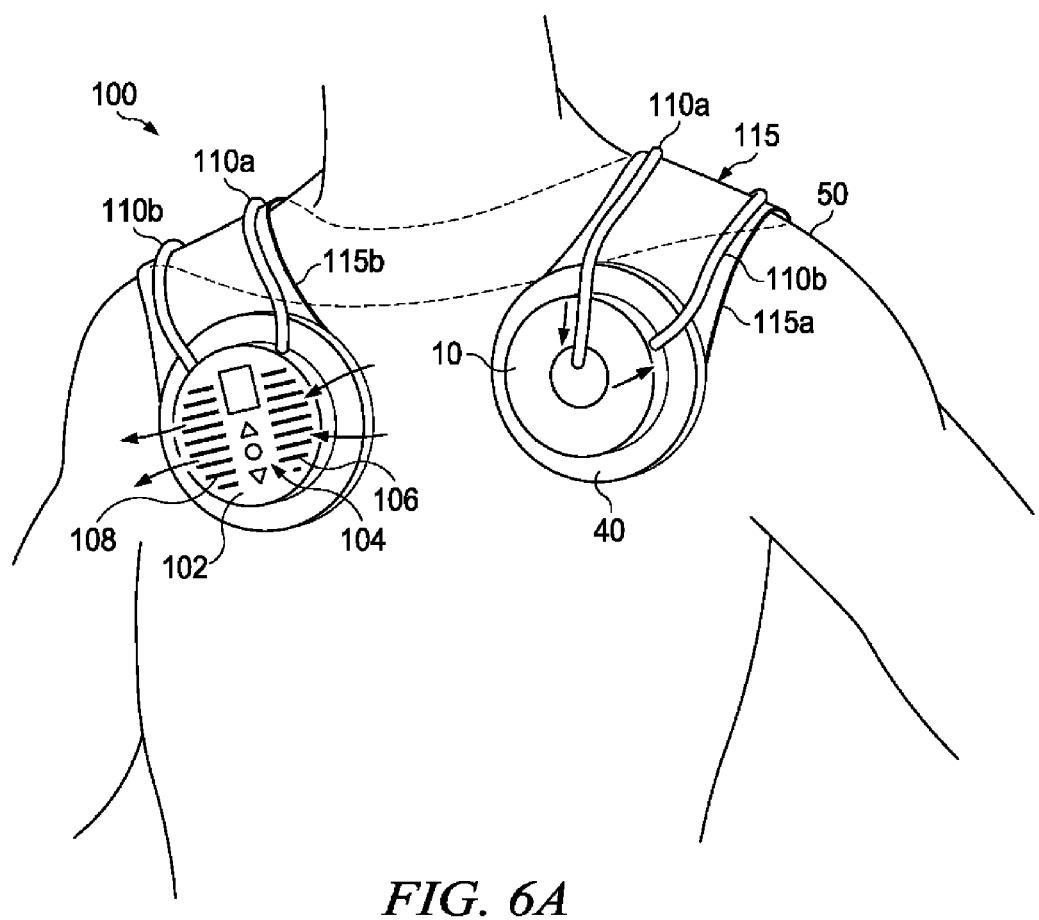
FIG. 6A illustrates a patient and shows an alternative strap or harness that may be attached to the patient to secure the ECA and the PCM heat accumulation structure in a desired position relative to a cooling system.
Figure 6B:
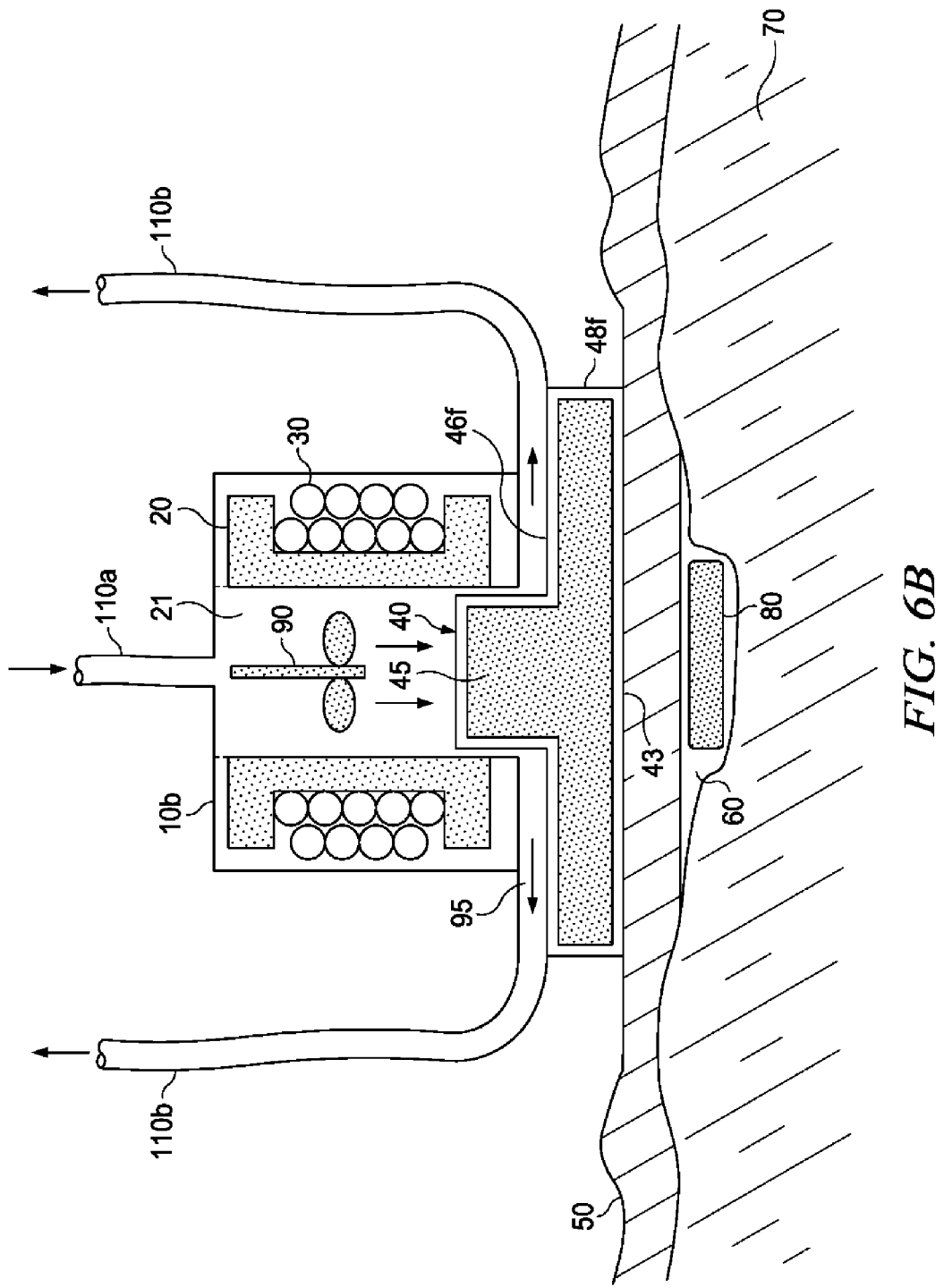
FIG. 6B is a cross-sectional view similar to the embodiment of FIG. 2, with the addition of cooling tubes of a cooling system similar to the embodiment of FIG. 6A.

FIGS. 6A and 6B schematically illustrate a TET system 100 that cools the ECA 10 by providing a flow of cooling air that passes through airflow inlets and outlets that are disposed at a distance away from the ECA 10. As illustrated in FIG. 6A, an alternative strap 115 (or harness), similar to the strap 15 illustrated in FIG. 3, can be attached to a patient to secure the ECA 10 and the PCM heat accumulation structure 40 in proper position relative to the patient's dermal layer 50. In the exemplary embodiment of FIG. 6A, the strap 115 has two opposing ends with one strap end 115a supporting the ECA 10 and the PCM heat accumulation structure 40 and the other strap end 115b supporting a housing 102 that can support a battery (not shown) that provides power to the ECA 10 via wiring (not shown) extending along the length of the strap 115 to connect the battery to the ECA 10. The housing 102 at the other strap end 115b can also support a control interface and display 104 that allows an operator to program and control the operation of the TET system 100. The housing 102 can also support a venting inlet 106 and venting outlet 108 fluidly communicating with tubing 110a and 110b that extend the length of the strap 115 to connect the venting inlet 106 and venting outlet 108 to the ECA 10 to provide a pathway for a flow of cooling air. The venting inlet 106 can fluidly communicate with an end of the tubing 110a to direct an incoming flow of air from the venting inlet 106 to the opposing end of the tubing 110a that connects to the ECA 10 to deliver the flow of cooling air to the interior space 21 of the bobbin 20 of the ECA 10 (shown in FIG. 6B). In an opposite manner, a return flow of the cooling air, warmed after passing through the interior space 21 of the bobbin 20, exits the ECA 10 and passes through the tubing 110b to be delivered to the venting outlet 108. A fan (not shown in FIG. 6A) can be provided near or at the venting inlet 106 or venting outlet 108 to propel the flow of cooling air through the cooling system defined by the venting inlet 106, the tubings 110a and 110b, and the venting outlet 108. The fan can also be provided near the ECA 10, within the interior space 21 of the bobbin 20 as illustrated by the fan 90 in FIG. 6B, or provided adjacent to the interior space where the inlet tubing 110a meets the interior space of the bobbin 20. In the embodiment illustrated in FIG. 6A, a single tubing 110a delivers the flow of cooling air to the ECA 10 and a single tubing 110b directs the now-warmed flow of cooling air away from the ECA. As can be appreciated, multiple tubes or pathways can be used to direct the flow of cooling air to and from the ECA 10, such as is shown in FIG. 6B where two tubings 110b are provided to direct the exit of the now-warmed flow of cooling air away from the ECA 10. As can also be appreciated, the flow of cooling air can achieve thermal communication and cool the ECA 10 by passing along the exterior of the coil 30 wrapped about the bobbin 20 or along another thermally effective pathway through or adjacent to the ECA 10. As can be further appreciated, the exit of the flow of cooling air from the ECA 10 can be immediately vented out of the cooling system by placing the venting outlet 108 at the strap end 115a with the venting outlet 108 positioned on or near the ECA 10.

Figure 7A:
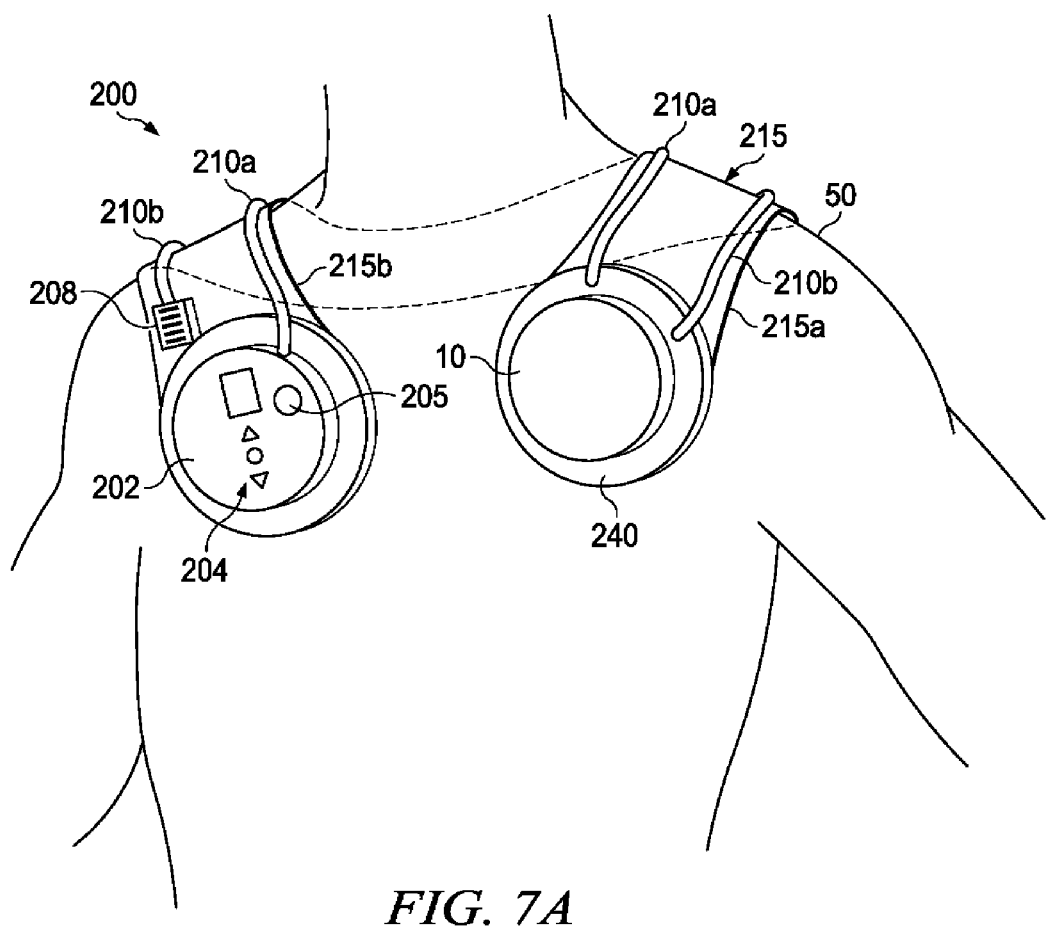
FIG. 7A illustrates a patient and shows yet another alternative strap or harness that may be attached to the patient to secure the ECA and the PCM heat accumulation structure in a desired position relative to an alternative cooling system.
Figure 7B:
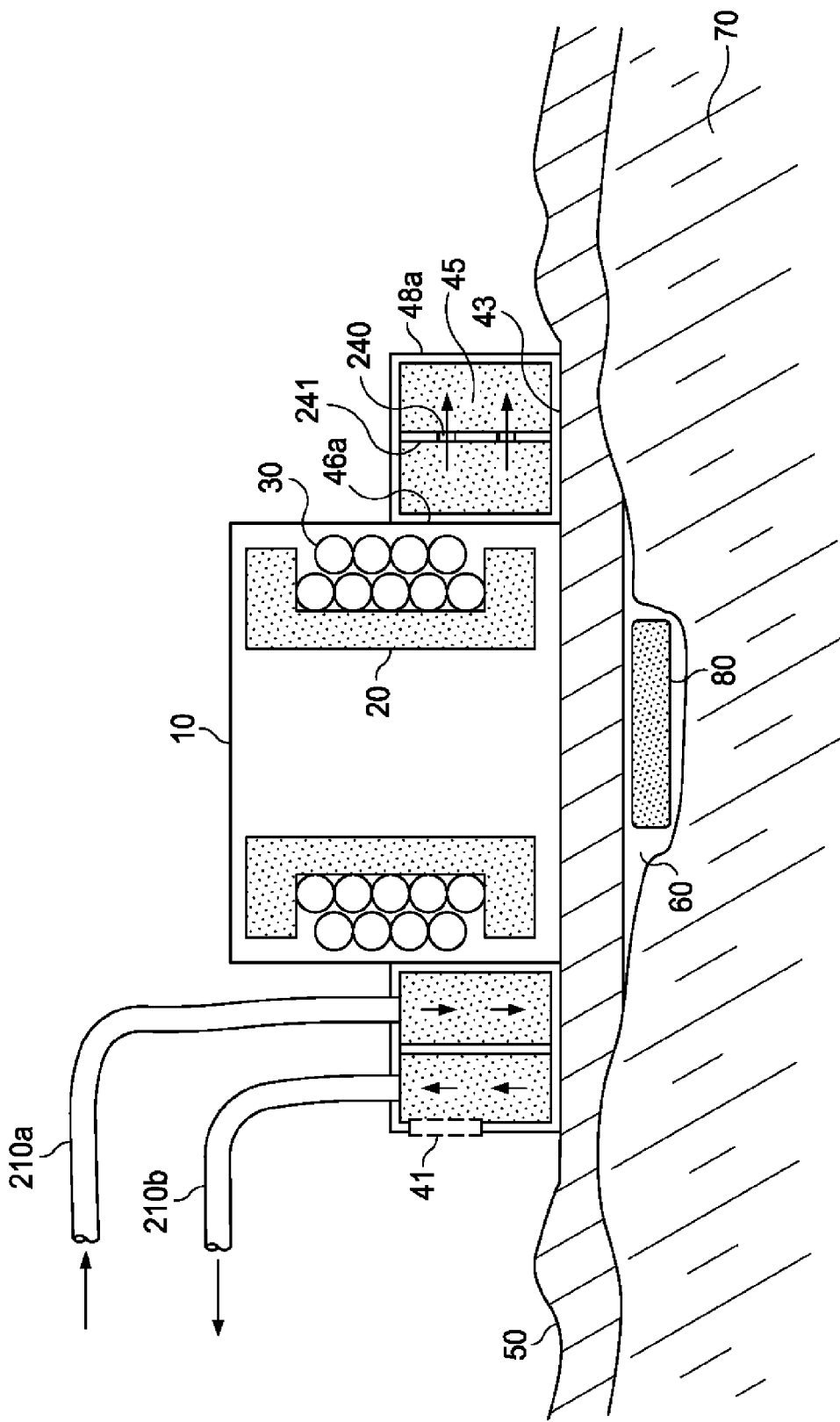
FIG. 7B is a cross-sectional view similar to the embodiment of FIG. 1A, with the addition of cooling tubes of a cooling system similar to the embodiment of FIG. 7A.

FIGS. 7A and 7B illustrate an alternative cooling system that delivers a flow of liquid to resupply the material within the PCM heat accumulation structure 240 as the material within the PCM heat accumulation structure 240 undergoes a phase change to produce a gas. FIG. 7A schematically illustrates a TET system 200 having an alternative strap 215 (or harness) similar to the strap 15 illustrated in FIG. 3. The strap 215 can be attached to a patient to secure the ECA 10 and the PCM heat accumulation structure 240 in proper position relative to the patient's dermal layer 50. In the exemplary embodiment of FIG. 7A, the strap 215 has two opposing ends with one strap end 215a supporting the ECA 10 and the PCM heat accumulation structure 240 and the other strap end 215b supporting a housing 202 that can support a battery (not shown) that provides power to the ECA 10 via wiring (not shown) extending along the length of the strap 215 to connect the battery to the ECA 10. The housing 202 at the other strap end 215b can also support a control interface and display 204 that allows an operator to program and control the operation of the TET system 200. The housing 202 can also support an internal reservoir (not shown) with a reservoir inlet port 205 that allows refilling of the internal reservoir as needed. The internal reservoir can fluidly communicate with tubing 210a which extends the length of the strap 215 to connect the internal reservoir to the PCM heat accumulation structure 240 to provide a pathway for a flow of cooling liquid. The tubing 210a can direct the flow of cooling liquid to an interior of the PCM heat accumulation structure 240 to cool the ECA 10 (as shown in FIG. 6B). After cooling the ECA 10, and undergoing a phase change, the cooling liquid changes to a gas that is directed out of the PCM heat accumulation structure 240 to tubing 210b which directs the gas to a terminal end of the tubing 210b at a venting outlet 208. As illustrated in FIG. 7B, the PCM heat accumulation structure 240 can be configured to have an internal partition 241 that directs the flow along a tortuous pathway through the interior PCM heat accumulation structure 240 to maximize the cooling provided to the ECA 10. In the exemplary embodiment of FIG. 7B, the tortuous pathway has the inflowing liquid enter an inner portion of the PCM heat accumulation structure 240 that is adjacent to the ECA 10, with the flow compelled to flow along a semi-circular path about the PCM heat accumulation structure 240 until reaching vent holes 242 that allow the flow to move to an outer portion of the PCM heat accumulation structure 240 surrounding the inner portion, with the tortuos pathway continuing as the flow traverses a semi-circular pathway back to exit the PCM heat accumulation structure 240 via the tubing 210b for venting at the venting outlet 208. As can be appreciated, a fan (not shown in FIG. 7A or 7B) can be provided near the internal reservoir or near or within the tortuous pathway within the PCM heat accumulation structure 240 to propel the flow of liquid or gas through the cooling system defined by the internal reservoir, the tubings 210a and 210b, the PCM heat accumulation structure 240, and the venting outlet 208. In the embodiment illustrated in FIG. 7A, a single tubing 210a delivers the flow of cooling liquid to the PCM heat accumulation structure 240 and a single tubing 210b directs the now-warmed flow of cooling gas away from the PCM heat accumulation structure 240. As can be appreciated, multiple tubes or pathways can be used to direct the flows to and from the PCM heat accumulation structure 240. As can also be appreciated, the flow passing through the PCM heat accumulation structure 240 achieve thermal communication and cool the ECA 10 by passing through a variety of tortuous pathways through the PCM heat accumulation structure 240 or by passing through a direct non-tortuous pathway through the PCM heat accumulation structure 240. As can be further appreciated, the exit of the flow of cooling gas from the PCM heat accumulation structure 240 can be immediately vented out of the cooling system by placing the venting outlet 208 at the strap end 215a with the venting outlet 208 positioned on or near the PCM heat accumulation structure 240.

Figure 8:
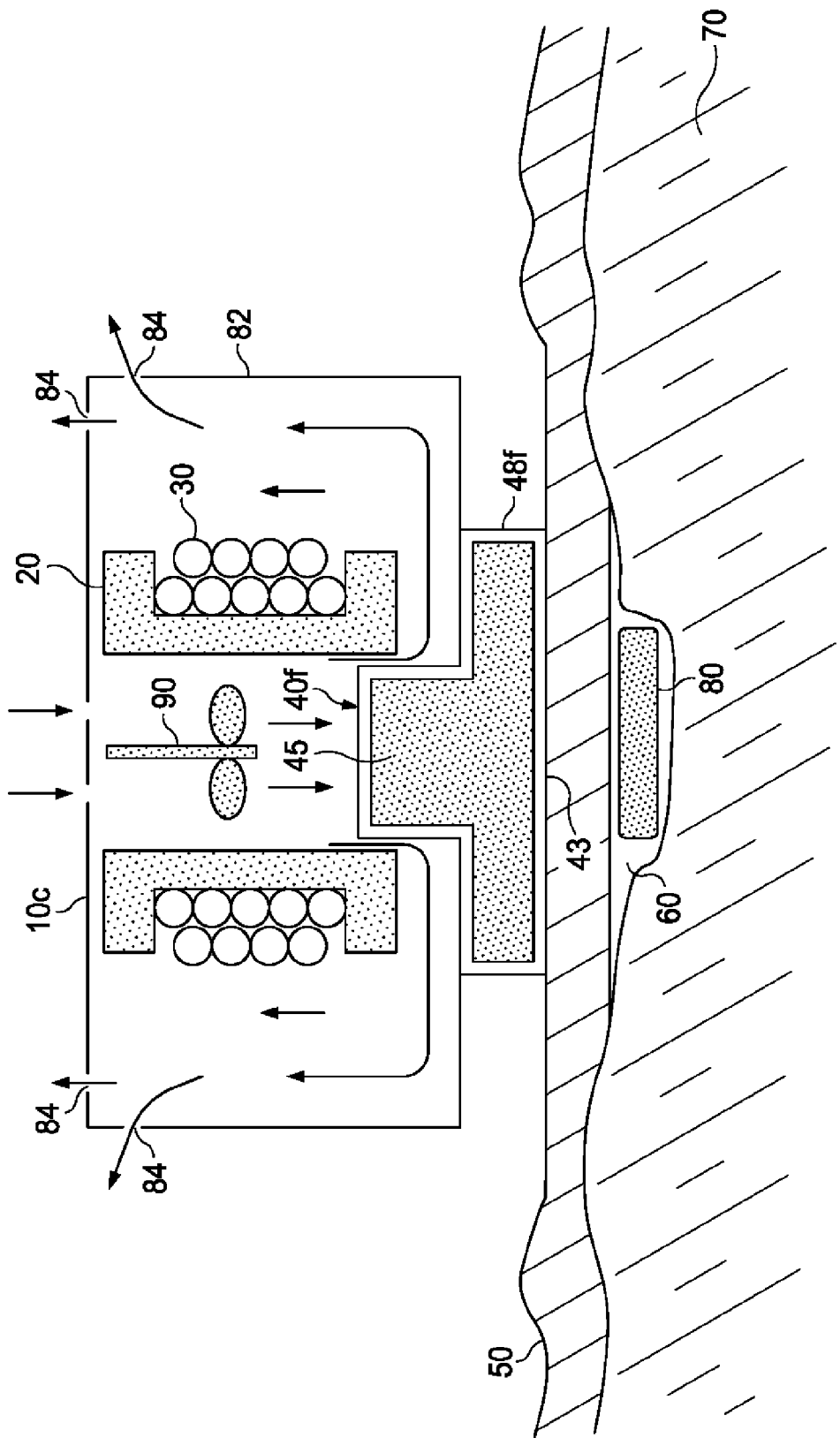
FIG. 8 is a cross-sectional view similar to the embodiment of FIG. 2, with the addition of vents of an expanded housing.

FIG. 8 is a cross-sectional view of an alternate cooling system in accordance with embodiments of the present invention. In this embodiment, an ECA 10c includes a cooling fan 90 disposed to remove thermal energy, similar to the embodiment illustrated in FIG. 2. However, in FIG. 8, the ECA 10c comprises a housing 82 with a larger diameter than the housing shown in FIG. 2. This expanded housing and additional vents 84 allows for more efficient use of convection air flow to cool the primary coil 30 of the ECA 10c. The PCM 45 contained in the enclosure may be optionally included or omitted in various embodiments.

Referring to the exemplary embodiment illustrated in FIG. 8, the additional vents and the inclusion of a spacing between the exterior of the coil and the inside of the expanded housing advantageously allows the cooling fluid to simultaneously circulate about the interior and exterior of the coil. As can be appreciated, the flow of the cooling fluid can be directed to first pass through the interior of the coil and then be directed to change direction to pass over the exterior of the coil. Alternatively, the cooling fluid can be directed to split and simultaneously flow in the same direction over the interior and exterior of the coil.

In one or more of the embodiments discussed above, the PCM structure can be used as an interlock, so users cannot charge an implanted device without such a PCM structure in place. Such interlocks can be implemented by incorporating a switch into a portion of the ECA, where the switch is actuated when the PCM structure is attached to the ECA.

Yet another modification which can be made to any of the embodiments discussed herein involves the incorporation of a thermal monitoring capability into a TET charging system, where the thermal monitoring capability is employed to determine when a spent PCM structure (i.e., a structure whose PCM is approaching or has reached its heat capacity, and is about to or has changed state) and should be replaced with a fresh PCM structure (i.e., a structure whose PCM is below the phase change temperature, and is thus ready to absorb thermal energy). Such thermal monitoring can be applied to one or more of the PCM material, the ECA, or tissue proximate the implanted device. Many different types of sensors, including but not limited to infrared thermometers and thermocouples, can be used for such thermal monitoring purposes. Where a temperature of the PCM material is being monitored, note that the PCM will gradually increase in temperature until the temperature required for the phase change is met, will then maintain a generally constant temperature during the phase change, and will experience temperature increases again after the phase change. A rise in temperature after a plateau is thus indicative that a PCM is spent. Where a temperature of the ECA or tissue is being monitored, note that once a normal operating temperature has been reached, the heat absorbing capacity of the PCM will enable the ECA/tissue to maintain a generally constant temperature until the PCM is spent. Thus, a rise in temperature after a plateau is also indicative that a PCM is spent.

It should also be recognized that while the above description has emphasized that the secondary coil is used to charge a rechargeable energy source (e.g. a rechargeable battery or capacitor), that the concepts disclosed herein can also be employed in connection with implanted medical devices that include no such rechargeable energy source. Such implanted medical devices would only be energized when the ECA is providing energy to the secondary coil, however, such an embodiment would likely be used where the implanted medical device was used infrequently.

Some of the exemplary embodiments discussed above have emphasized PCM materials that act as a heat sink as the material transitions from a solid to a liquid. It should be recognized that materials transitioning from a liquid to a gas or vapor, or from a solid to a gas or vapor, could also be used as a heat sink, so long as the temperature associated with the phase change was in the desired range. Such materials function as a heat sink due to the latent heat of vaporization, rather than the latent heat of fusion. As can be appreciated, a PCM that undergoes a phase change can produce an increase in volume or pressure (e.g., in a phase change from a liquid to a solid, a solid to a gas, or a liquid to a gas) and any container housing such a PCM must be designed to take into account the increased volumes and pressures that would accompany such a phase change. In any of the embodiments described herein, a vent or pressure-relief valve can be installed in the container housing a PCM to relieve increases in pressure or volume. Likewise, the container housing a PCM can be configured to have an expanding portion of the container that expands to compensate for increases in pressure or volume.

While the embodiments discussed above have focused on thermally coupling the PCM to the patient's tissue, it should be noted that the concepts disclosed herein also encompass embodiments wherein the PCM is thermally isolated from the patient's tissue, such that the PCM is used as a heat sink only for the ECA. Such an embodiment will prevent thermal energy from the ECA from being absorbed into the patient's tissue, thus enabling the tissue to safely absorb more thermal energy from the implanted medical device during charging or supply of electrical power to the implanted device.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

What is claimed is:

1. A transcutaneous energy transfer system for providing power to an implanted device, the system comprising:
   a strap having opposing first and second ends;
   an external charging device mounted on the first end of the strap, the external charging device having a primary induction coil and a surface configured to face the implanted device to provide energy from the primary induction coil to the implanted device, the primary induction coil defining an inner volume at a center of the primary induction coil;
   a cooling system mounted on the second end of the strap, the cooling system having an air inlet and an air outlet;
   a phase change material disposed at the first end of the strap in thermal communication with the external charging device; and
   a tubing extending between the first and second ends of the strap, an interior lumen of the tubing fluidly communicating with the inner volume of the external charging device and at least one of the air inlet and the air outlet of the cooling system.

2. The system of claim 1, further comprising a fan disposed within at least one of the external charging device and the cooling system.

3. The system of claim 1, further comprising at least one of a control interface, a display, and a battery in signal communication with at least one of the external charging device and the cooling system.

4. The system of claim 1, wherein a phase transition point of the phase change material is less than a predetermined temperature, the predetermined temperature being a temperature at which tissue damage can occur from a timed exposure to a heat generated by at least one of the external charging device and the implanted device, the time exposure being a time over which energy is provided to the implanted device.

5. The system of claim 4, wherein the external charging device and an enclosure containing the phase change material each have external surfaces configured to define an alignment with each other.

6. The system of claim 4, wherein the phase change material is a composite of a plurality of phase change materials, each of the plurality of phase change materials having a different temperature at which a phase change occurs.

7. A method of cooling an external charging device configured to be disposed on the skin of a human body, the method comprising:
   delivering a flow from one side of the body to the other via a tubing, the flow including at least one of an airflow phase change material and a liquid phase change material; and
   cooling a surface of the external charging device with the flow.

* * * * *